(12) United States Patent
Hooi

(10) Patent No.: US 8,672,872 B2
(45) Date of Patent: Mar. 18, 2014

(54) SANITARY PRODUCT

(75) Inventor: (Alex) Yu Sing Hooi, London (GB)

(73) Assignee: Calla Lily Personal Care Ltd, London (GB)

( * ) Notice: Subject to any disclaimer, the term of this patent is extended or adjusted under 35 U.S.C. 154(b) by 679 days.

(21) Appl. No.: 11/920,481

(22) PCT Filed: May 17, 2006

(86) PCT No.: PCT/GB2006/001802
§ 371 (c)(1),
(2), (4) Date: May 27, 2008

(87) PCT Pub. No.: WO2006/123132
PCT Pub. Date: Nov. 23, 2006

(65) Prior Publication Data
US 2009/0131852 A1 May 21, 2009

(30) Foreign Application Priority Data

May 17, 2005 (GB) .................................. 0509979.1

(51) Int. Cl.
*A61F 13/20* (2006.01)
(52) U.S. Cl.
USPC ............ 604/11; 604/385.17; 604/385.18; 604/904; 604/12; 604/13; 604/14; 604/15; 604/16; 604/17; 604/18; 604/379; 604/380
(58) Field of Classification Search
USPC ........... 604/385.17, 385.18, 904, 11–18, 604/379–380, 385.01, 385.201
See application file for complete search history.

(56) References Cited

U.S. PATENT DOCUMENTS

| 2,092,346 A | | 9/1937 | Arone |
| 2,138,626 A | | 11/1938 | Copen |
| 2,331,355 A | * | 10/1943 | Strongson ..................... 604/365 |

(Continued)

FOREIGN PATENT DOCUMENTS

| DE | 29611480 | 12/1996 |
| DE | 29620118 | 3/1998 |

(Continued)

OTHER PUBLICATIONS

English translation of WO 94/22405, Aug. 2008.*

(Continued)

*Primary Examiner* — Tatyana Zalukaeva
*Assistant Examiner* — Ginger T Chapman
(74) *Attorney, Agent, or Firm* — Knobbe Martens Olson & Bear LLP

(57) ABSTRACT

A sanitary product for use by women for the absorption of menstrual fluid, having a plug and a pad joined by a sheath. The plug is substantially cylindrical so that is fits comfortably in a vaginal cavity. The pad remains outside the vaginal cavity, but has an absorbent layer on an inward side proximal to the plug and a liquid impermeable layer on an outward side. In use, a wearer can insert a finger into the sheath from the outward side of the pad to assist with insertion of the plug into the vaginal cavity. A string is provided that extends inside the sheath from the outward end of the plug to aid removal of the product. A line of weakness extends along the major axis of the pad, about which the pad is disposed to fold in use.

26 Claims, 5 Drawing Sheets

(56) References Cited

U.S. PATENT DOCUMENTS

| | | | |
|---|---|---|---|
| 2,670,736 A | | 3/1954 | Dunkelberger |
| 2,733,714 A | * | 2/1956 | Haas ............................... 604/14 |
| 3,037,506 A | * | 6/1962 | Penksa .................... 604/385.18 |
| 3,058,469 A | * | 10/1962 | Crockford ..................... 604/363 |
| 3,420,234 A | * | 1/1969 | Phelps .......................... 604/377 |
| 3,674,029 A | * | 7/1972 | Bates et al. .................. 604/366 |
| 3,690,321 A | * | 9/1972 | Hirschman et al. ........... 604/359 |
| 3,905,372 A | * | 9/1975 | Denkinger .................... 604/359 |
| 3,946,737 A | * | 3/1976 | Kobler .................... 604/385.18 |
| 4,627,848 A | | 12/1986 | Lassen et al. |
| 5,113,873 A | * | 5/1992 | Boarman ....................... 128/830 |
| 5,180,059 A | * | 1/1993 | Shimatani et al. ............ 206/440 |
| 5,193,684 A | * | 3/1993 | McDonald .................... 206/581 |
| 5,290,262 A | | 3/1994 | Vukos et al. |
| 5,361,779 A | | 11/1994 | Wilson, III |
| 5,383,868 A | | 1/1995 | Hyun |
| 5,389,181 A | | 2/1995 | Vukos et al. .................. 156/264 |
| 5,690,625 A | | 11/1997 | Widlund .................... 604/385.18 |
| 5,827,256 A | * | 10/1998 | Balzar ...................... 604/385.18 |
| 5,891,123 A | * | 4/1999 | Balzar ...................... 604/385.18 |
| 6,059,763 A | | 5/2000 | Brown ....................... 604/385.1 |
| 6,348,047 B1 | | 2/2002 | Harper |
| 6,840,927 B2 | | 1/2005 | Hasse |
| 6,863,664 B2 | | 3/2005 | Wada |
| 6,939,333 B1 | * | 9/2005 | Franklin, Jr. ............. 604/385.17 |
| 7,112,192 B2 | | 9/2006 | Hasse |
| 2004/0024376 A1 | * | 2/2004 | Ohba ....................... 604/385.17 |
| 2004/0147893 A1 | * | 7/2004 | Mizutani et al. ......... 604/385.17 |
| 2004/0147897 A1 | * | 7/2004 | Mizutani et al. ......... 604/385.17 |
| 2004/0225272 A1 | | 11/2004 | Karapasha |
| 2005/0055003 A1 | | 3/2005 | Bittner |
| 2008/0077105 A1 | | 3/2008 | Hooi |
| 2012/0197230 A1 | | 8/2012 | Hooi |

FOREIGN PATENT DOCUMENTS

| | | | | |
|---|---|---|---|---|
| EP | 0 104 039 | | 3/1984 | |
| EP | 136524 A1 | * | 4/1985 | |
| EP | 1 206 925 A2 | | 5/2002 | |
| FR | 2590161 | * | 11/1985 | .............. A61F 13/18 |
| FR | 2 653 328 | * | 10/1989 | .............. A61F 13/46 |
| FR | 2653328 A | * | 10/1989 | .............. A61F 13/46 |
| JP | 08-112311 A | | 5/1996 | |
| JP | 2000-237234 | * | 9/2000 | .............. A61F 13/20 |
| JP | 2003-10243 | | 1/2003 | |
| JP | 2005-177074 A | | 7/2005 | |
| WO | WO 94/22405 | * | 10/1994 | .............. A61F 13/15 |
| WO | WO 02/058611 | | 8/2002 | |
| WO | WO 03/015676 A2 | | 2/2003 | |

OTHER PUBLICATIONS

International Search Report and Written Opinion for PCT/GB2006/001802.

U.S. Appl. No. 10/582,445, filed Sep. 25, 2006, Hooi, Final OA, Oct. 26, 2010.

U.S. Appl. No. 10/582,445, filed Sep. 25, 2006, Hooi, Response to Non-Final OA, Aug. 25, 2010.

U.S. Appl. No. 10/582,445, filed Sep. 25, 2006, Hooi, Non-Final OA, Jun. 25, 2010.

U.S. Appl. No. 10/582,445, filed Sep. 25, 2006, Hooi, Amendment and Response to Final Office Action, May 20, 2010.

U.S. Appl. No. 10/582,445, filed Sep. 25, 2006, Hooi, Interview Summary, Apr. 5, 2010.

U.S. Appl. No. 10/582,445, filed Sep. 25, 2006, Hooi, Final Office Action, Jan. 27, 2010.

Final Office Action mailed by the U.S. Patent and Trademark Office on Nov. 2, 2011 for U.S. Appl. No. 10/582,445, filed Sep. 25, 2006.

* cited by examiner

SANITARY PRODUCT

CROSS REFERENCE TO RELATED APPLICATIONS

The present application is a National Phase Application of International Application No. PCT/GB2006/001802, filed May 17, 2006, which claims priority to Great Britain Patent Application No. 0509979.1, filed May 17, 2005, which applications are incorporated herein fully by this reference.

FIELD OF THE INVENTION

This invention relates to a sanitary product. More specifically, but not exclusively, the invention relates to a sanitary product for use by women for the absorption of menstrual fluid, the product comprising a combined tampon and sanitary towel.

BACKGROUND TO THE INVENTION

During menstruation, women commonly choose to use either a tampon or a sanitary towel to absorb menstrual fluid. However, hybrid sanitary products, comprising both a tampon (e.g. an internally worn plug) and a sanitary towel (e.g. an externally worn pad) have also been suggested. These hybrid sanitary products are expected to begin to replace the use of separate tampons and sanitary towels over coming years.

For example, patent publications U.S. Pat. No. 3,420,234, U.S. Pat. No. 3,690,321 and JP2003-010243 all describe sanitary products comprising combined internally worn plugs and externally worn pads of various shapes and designs. However, all these sanitary products suffer from a number of disadvantages. In particular, there are significant difficulties associated with removal and disposal of these products after use.

The sanitary product described in U.S. Pat. No. 3,420,234 has an internally worn plug joined to an externally worn pad. This publication does not describe removal of the sanitary product after use in any detail. However, it is evident that the wearer is required to handle the sanitary product directly during removal. Typically, the pad might be grasped and used to pull the plug out of the vagina. It is most likely that the wearer will grasp edges of the pad. As force is exerted on the pad by the wearers grasp, the wearer's fingers are likely to crush the edges of the pad and/or the wearer's fingers will extend around the pad to a surface of the pad facing the vagina in use. Hence, it is very likely that the wearer's hands will come into contact with the surface of the pad facing the vagina in use, which is likely to be soiled. This is unpleasant for the wearer. It is also unhygienic.

The pad described in U.S. Pat. No. 3,420,234 is also unlikely to be able to fully support the plug as the pad is pulled away from the body and the plug exits the vaginal cavity. This problem is exacerbated by the weight of menstrual liquid absorbed by the plug during use and the likely softening of materials from which the plug and pad are made by the absorbed liquid. One option is therefore for the wearer to grasp the soiled plug as it exits the vaginal orifice. This is clearly undesirable. Alternatively, the plug is liable to hang down from the pad as it exits the vaginal cavity, making the sanitary product cumbersome to manipulate and making it likely that the wearer's hands will nonetheless unintentionally come into contact with the soiled plug. So, removal and disposal of this sanitary product after use is far from satisfactory.

U.S. Pat. No. 3,690,321 describes a sanitary product similar to that described in U.S. Pat. No. 3,420,234. However, this publication mentions that possibility of providing a string attached to the pad to facilitate removal. The string may enable the wearer to avoid directly grasping the pad during removal. However, the sanitary product still remains cumbersome after removal and inadvertent contact with soiled parts of the used sanitary product seems likely, even when the wearer holds it by a string. It should be borne in mind that the plug and pad combination may be larger and more unwieldy than a conventional tampon that a wearer might be used to removing with an attached string. Again, removal and disposal of this sanitary product after use can therefore be unpleasant and unhygienic.

JP2003-010243 describes a sanitary product comprising an internally worn plug attached to an externally worn pad using a finger sack that opens through the pad. The plug can be manipulated by a wearer's finger inserted into the sack from a side of the pad facing away from the body in use. The sack is double skinned and a string attached to the plug passes between the skins of the sack. It is unclear whether or not this string can be grasped directly by the wearer to assist with removal of the plug. Regardless, this publication does not describe removal of the sanitary product and it is again clear that the cumbersome nature of the sanitary product makes it likely that the wearer's hands will come into contact with the soiled parts of the sanitary product during removal. In this case, the problem is exacerbated by the flexible nature of the sack, which leaves the plug very free to move in relation to the pad in an unwieldy manner.

So, none of these existing hybrid sanitary products are capable of reliable hygienic removal and disposal. The present invention seeks to overcome this problem.

SUMMARY OF THE INVENTION

According to the present invention, there is provided a sanitary product for insertion into a human vagina, the product comprising an internally worn absorbent plug and an externally worn absorbent pad, wherein the pad has a line of weakness about which it is disposed to fold.

So, the pad has a tendency to fold in use, e.g. as it is manipulated by a wearer of the sanitary product. This is important, as it can encourage folding of the pad during removal of the plug.

More specifically, as the plug is removed from the vagina, a wearer typically grasps the pad from a surface of the pad facing away from the vagina in use. Under the force of the wearer's grasp, the pad has a tendency to fold around the line of weakness toward the surface of the pad facing toward the vagina in use. This folding of the pad towards the vagina can reduce the likelihood of the wearer touching the surface facing toward the vagina in use. As this surface is typically soiled during use and the surface facing away from the vagina in use is generally relatively clean, hygiene can therefore be maintained.

Furthermore, as the internally worn plug is removed from the vagina, it can be accommodated by the folded pad. In other words, the grasping of the pad as the plug is pulled out of the vagina can cause the pad to fold over the plug. Indeed, the plug can be enclosed by the pad. Again, as the plug is generally soiled, but the surface of the pad grasped by the wearer is generally relatively clean, the likelihood of the wearer touching the plug during removal of the sanitary product is reduced and hygiene is maintained.

In the context of this invention, internally worn means inside the vaginal cavity. In other words, it means inwardly of the vaginal orifice. Externally worn means outside the vaginal cavity. In other words, it means outwardly of the vaginal orifice.

It is actually preferred that the pad of the invention is worn in the vulva, e.g. between the labia majora. The vulva is effectively a narrow trough passing over the opening to the vaginal cavity. Another advantage of the invention is that the line of weakness can allow the pad to conform more closely to the vulva. In other words, the pad can fold along the vulva in use and fit closely to the shape of the vulva. This improves comfort and can help to prevent excess menstrual fluid leaking between the pad and the vagina. It can also help to hold the sanitary product in place. In other words, displacement of the product once fitted is discouraged by the close fit to the vulva.

In order for the pad to conform to the vulva, it is desirable for the line of weakness to run in the same direction as the length of the vulva in use. The pad is usually longest in a direction the same as the length of the vulva in use. So, it is preferred that the line of weakness runs along the length of the pad. More specifically, it is preferred that the line of weakness is substantially coincident with a major axis of the pad.

Nonetheless, other configurations are possible. For example, the line of weakness may be transverse to the length of the pad. This allows the pad to fold around an axis transverse to the vulva in use. Again, the pad can therefore fold around the plug during removal of the plug. However, the pad may also be folded away from the vulva by a user whilst in use. For example, a portion of the pad covering the opening of the urethra may be folded away from the body in use, allowing urination whilst the sanitary product is in place. So, the line of weakness may extend across the pad at a position toward the plug from the (intended or likely) location of the opening of the urethra in use. Indeed, the position of the line of weakness might be at the location of the plug. Alternatively or additionally, the position might be at the widest part of the pad, e.g. along the minor axis of an elliptical pad. The line of weakness might also be transverse or even perpendicular to the major axis of the pad.

Typically, the pad is roughly symmetric about its major axis. So, the line of weakness may substantially bisect the pad. This is particularly useful as it allows the pad to fold evenly into a fully folded condition at which the surface of the pad facing the vagina in use is completely covered by the surface of the pad facing away from the vagina in use.

It can be appreciated that the pad may have two or more lines of weakness about which it is disposed to fold. These might be oriented at right angles to one another, e.g. in a cross. This might encourage the pad to collapse in quadrants defined by the lines.

The line(s) of weakness might typically be less stiff than the pad to either side of the line (e.g. substantially the rest of the pad) to encourage the pad to fold around the line. It is preferred that the line(s) of weakness allow(s) the pad to fold both away and toward the surface of the pad in contact with the vagina in use. This allows the pad both to fold toward that surface for hygienic removal and disposal of the sanitary product and to fold away from that surface to conform to the vulva.

In one example, the line(s) of weakness may be (a) crease (s). Creases are relatively straightforward to provide during manufacture. They might be glued or stitched into an otherwise flat pad for example. However, it is particularly preferred that the line(s) of weakness is/are (a) line(s) of compression of the pad. For example, during manufacture, the pad might be compressed along the line to reduce the stiffness of the pad at the line. Again, other configurations are also possible, such as reducing the amount of material forming the pad at the line.

The plug and pad are preferably joined to one another by a sheath that opens through the pad such that a wearer's finger can be received in the sheath to assist insertion. So, the sanitary product can be thought of as a tampon attached to a sanitary towel by a tube. The tube passes through the sanitary towel to one end of the tampon. During insertion, a finger is inserted in the tube, i.e. through the pad, to the tampon such that the tampon can be easily manipulated.

It may be joined to an end of the plug that is nearest to the vaginal opening in use. It may also be joined to the pad and open through the pad so that a finger can be inserted into the sheath from the side of the pad that faces away from the body in use. This means that a wearer's finger can be inserted through the pad toward the end of the plug and movement of the inserted finger can easily manipulate the plug during insertion. Fitting the sanitary product of the invention is therefore far easier than fitting any previous combined sanitary product or, indeed, most tampons or sanitary towels. In particular, no separate introducer is needed and the product does not need to be held in place by adhesion to panties or by a belt.

It can be appreciated that the sheath typically opens through the pad at a point coinciding with the vaginal orifice in use. This is generally at a location fairly central to the pad. So, in many examples, the line(s) of weakness may extend(s) across the opening of the sheath through the pad. The line(s) of weakness are usually fairly straight. For simplicity of language, a line of weakness extending across the pad through the opening in a fairly straight direction is therefore considered as a single line in this document, although it can be appreciated that it could equally well be described as two lines, one on either side of the opening.

In order to optimise the ease with which the plug can be manipulated by a finger, the sheath is typically flexible. This allows the wearer's finger to easily move the plug relative to the pad. It is also preferred that the sheath terminates at the plug. More specifically, the sheath may extend all the way to the end of the plug nearest the vaginal opening in use. This allows the finger to reach the plug and directly manipulate it.

Another advantage of the invention is that, although the wearer's finger may enter the vaginal cavity during fitting, the finger is inside the sheath and does not come into direct contact with the vagina. This makes fitting the sanitary product of the invention clean and hygienic. Furthermore, use of the product is more acceptable for sexually inexperienced women or those with cultural objections.

In this regard, it is preferred that the sheath is liquid impermeable in a direction from the outside of the sheath to the inside of the sheath. In other words, the sheath may comprise a liquid impermeable membrane. For example, the sheath may comprise a tube of liquid impermeable material. Bodily or other liquids will not therefore pass through to the inside of the sheath and the inserted finger is protected.

In order to further protect the inserted finger, the sheath may be closed where it joins the plug. In one example, the perimeter of a tube forming the sheath may be joined to the plug, but the inside of the tube may effectively be open to the plug. However, it is preferred that the liquid impermeable membrane or tube of liquid impermeable material is itself closed at the end of the sheath that joins to the plug. This ensures that any liquid absorbed by the plug does not pass into the inside of the sheath.

Whilst it is useful to protect the inserted finger with a liquid impermeable membrane, it is desirable for liquid to be able to pass from the plug to the pad. It is therefore preferred that the sheath can pass liquid along its length from the plug to the pad. In other words, the sheath may comprise a tube of absorbent material. This allows excess fluid absorbed by the plug to be passed to the pad. The absorptive capacity of the product is therefore maximised and the size of the plug and pad can be minimised.

In a particularly preferred example, the sheath comprises a tube of liquid impermeable material inside a tube of absorbent material. This allows liquid to pass from the plug to the pad, but not into the inside of the sheath.

Although, as described below, the plug has a diameter smaller than that of an average conventional tampon, in order to have sufficient absorbency the plug has a relatively wide diameter in comparison to an average vaginal orifice. It is therefore preferred that the sheath has a smaller diameter than that of the plug. As the sheath is positioned at the vaginal orifice in use, this reduces pressure exerted on the vaginal orifice by the product and significantly improves comfort for the wearer.

Nonetheless, the sheath should be able to receive a finger, which is likely to have roughly the same or a slightly larger diameter than a small conventional tampon. It is therefore particularly preferred that the sheath is expandable in a radial direction to receive a finger during insertion of the product into the vagina. In particular, the sheath may be expandable in (only) a circumferential direction and not significantly in a longitudinal direction. (Significant elasticity in a longitudinal direction may be undesirable as it can lead to misplacement of the plug.) Preferably the sheath is resiliently expandable or elastic so that it returns to its smaller dimensions after removal of the wearer's finger and comfort is maintained. So, more specifically, the absorbent and liquid impermeable tubes may be elastic in only a circumferential direction.

Typically, the sheath extends for substantially 2.5 cm between an end of the plug and a surface of the pad closest to the plug. This length suitably positions the plug in the vaginal cavity.

As discussed above, the sanitary product can be removed by a wearer simply grasping the pad and pulling the sanitary product way from their body. This can draw the plug out of the vagina and cause the pad to fold around the plug. However, it is preferred that the product further comprises a string attached to the plug (or at least to the sheath near the plug) to assist removal of the plug from the vagina. It is particularly preferred that the string extends along the inside of the sheath. The string can then extend through the pad and be accessible to a wearer at the opening of the sheath through the pad.

When the wearer pulls on the string to remove the plug, the plug is first pulled outwardly from the vaginal cavity. The pad also tends to begin to fold around the plug. Importantly, the present invention recognizes that the sheath can invert to accommodate the plug. In other words, the string can be used to pull the plug into the sheath, which can turn inside out to accommodate the plug. The wearer therefore retrieves the plug inside the sheath and with the pad folded around the plug and sheath combination. There is therefore a very low chance of the wearer touching a soiled part of the sanitary product.

The term string is not intended to be limiting to any particular type of twine or thread. Rather, it is a general term referring to any usable cord or tail which the wearer can pull to extract the plug.

Typically, the pad comprises an absorbent layer and a liquid impermeable backing sheet. Conveniently, the backing sheet may be integral with the liquid impermeable material of the sheath. This ensures that no liquid passes through the pad to the side of the pad that faces outwardly in use. Similarly, the absorbent layer of the pad may be integral with the absorbent material of the sheath.

The dimensions of the pad can be selected for best fit and to provide sufficient absorptive capacity. In particularly preferred examples, any or all of the following dimensions can be used: the pad may be substantially 6.5 cm long; the pad may be substantially 5.5 cm wide; and/or the pad may be substantially 0.5 cm thick.

It is also preferred that the pad is a flat ellipse with one end wider than the other. The pad folds along its major axis in use and the irregular elliptical shape allows it to conform to the typical female anatomy.

The plug is similar in construction to a conventional tampon. For example, it typically comprises a wad of absorbent material. In other words, it is generally solid. Indeed, it is typically a solid cylinder, e.g. of compressed cotton.

As mentioned above, excess liquid may pass along the sheath from the plug to the pad. The present invention recognizes that, even when a sheath of small diameter is provided for comfort, this passing of liquid from the plug to the pad allows the size of the plug to be minimized. Indeed, sufficient absorption capacity can be provided in a plug substantially smaller than an average conventional tampon. It is therefore preferred that the plug is 4 cm in length or less and 2 cm in diameter or less.

In a particularly preferred embodiment, the plug is substantially 3.5 cm in length and 1.5 cm in diameter. Other than for women with large menstrual flow, these are the preferred maximum dimensions. Smaller dimensions may be suitable for women with light menstrual flow. It is therefore preferred that the plug is substantially 3.5 cm in length or less and 1.5 cm in diameter or less.

According to the present invention, there is also provided a method of manufacturing a sanitary product, the method comprising joining an internally worn absorbent plug to an externally worn absorbent pad and providing the pad with a line of weakness about which it is disposed to fold to produce the sanitary product described above.

Preferred embodiments of the present invention will now be described, by way of example only, with reference to the accompanying drawings.

DETAILED DESCRIPTION OF THE PREFERRED EMBODIMENTS

Figure 1:
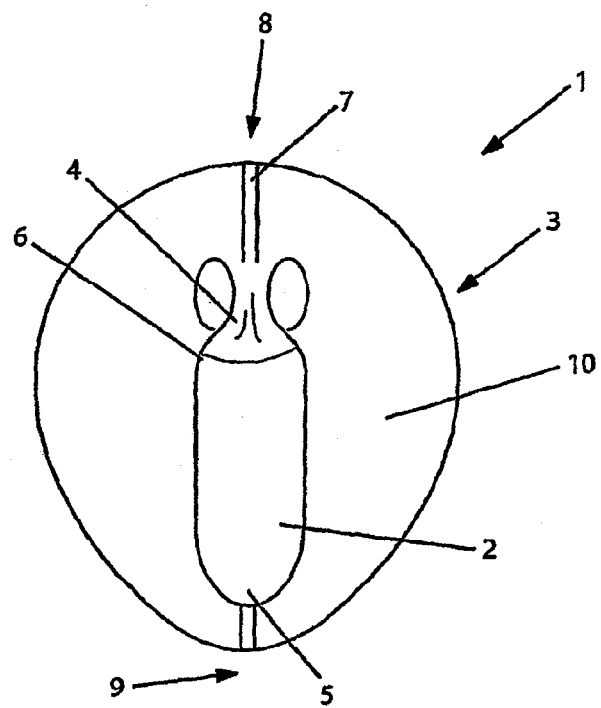
FIG. 1 is a front view of a sanitary product according to a preferred embodiment of the present invention.
Figure 2:
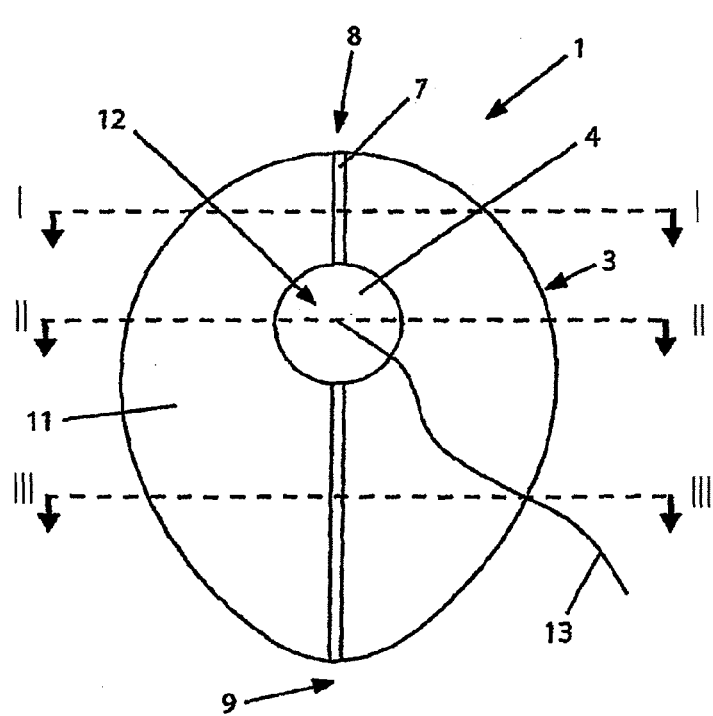
FIG. 2 is a rear view of the sanitary product of FIG. 1.
Figure 3:
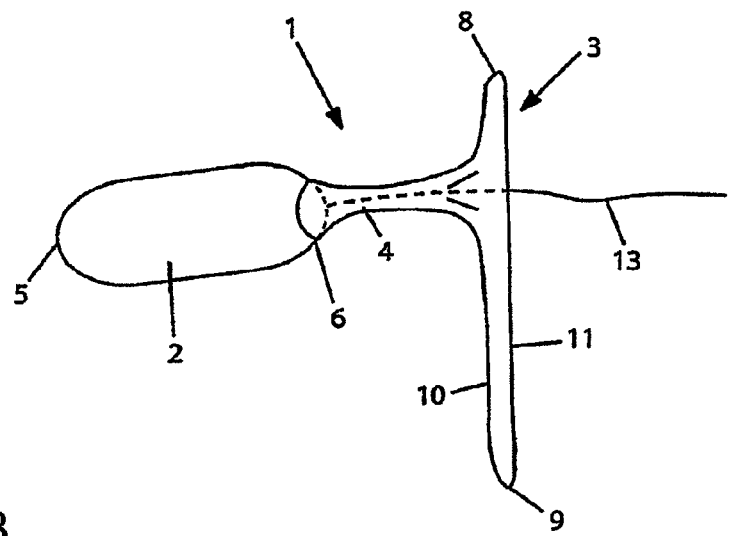
FIG. 3 is a side view of the sanitary product of FIG. 1.
Figure 4A:
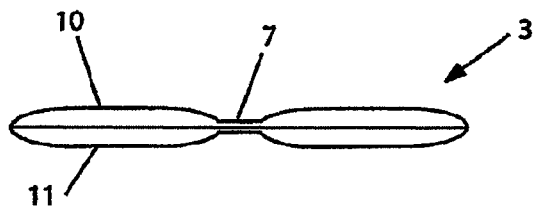
FIG. 4A is a cross sectional view of an externally wearable pad of the sanitary product of FIG. 1 along the line I-I in FIG. 2.
Figure 4B:
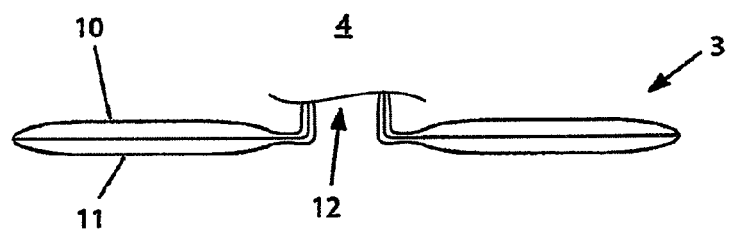
FIG. 4B is a cross sectional view of the pad of the sanitary product of FIG. 1 along the line II-II in FIG. 2.
Figure 4C:
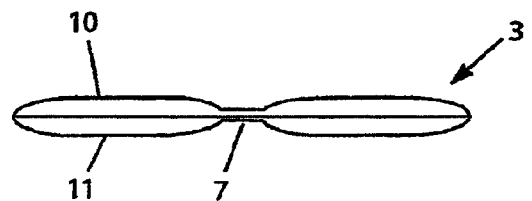
FIG. 4C is a cross sectional view of the pad of the sanitary product of FIG. 1 along the line III-III in FIG. 2.

Referring to FIGS. 1 to 4C, a sanitary product 1 according to a preferred embodiment of the present invention comprises a plug 2 and pad 3 joined by a sheath 4.

The plug 2 is substantially cylindrical so that it fits comfortably in a vaginal cavity. The end of the plug 2 that, in use, is inserted into the vaginal cavity first is referred to as the innermost end 5 of the plug 2. The end of the plug 2 that, in use, is inserted into the vaginal cavity last is referred to as the outermost end 6 of the plug 2. Both the innermost end 5 and outermost end 6 of the plug 2 are domed to ease insertion and removal of the plug 2 from the vaginal cavity. In another embodiment, the outermost end 6 is flat.

The plug 2 is typically around 3.5 cm in length and around 1.5 cm in diameter. In other embodiments, these dimensions might vary within reasonable limits; say 4 cm or less in length and 2 cm or less in diameter. However, for women with light menstrual flow, an intact hymen or no sexual experience, the plug 2 is generally shorter and of smaller diameter.

In this embodiment, the plug 2 is made from compressed cotton. For example, a sheet of compressed cotton may be cut and rolled into an appropriate shape. Other suitable materials and constructions may be used as desired.

Typically, the pad 3 is substantially a flat egg-shape or ovate. In other words, the perimeter of the pad 3 is an ellipse having one end (broad end 8) broader or wider than the other end (narrow end 9). The side of the pad 3 in contact with the vagina in use is referred to as the inward side 10 (shown as the front of the sanitary product 1 in FIG. 1) and the side of the pad 3 in contact with clothing in use is referred to as the outward side 11 (shown as the rear of the product 1 in FIG. 2).

The pad 3 has an absorbent layer on the inward side 10 and a liquid impermeable layer on the outward side 11. In this embodiment, the absorbent layer is made from compressed cotton and the liquid impermeable layer is made from a polymeric material. Other suitable materials may be used as desired.

The pad 3 is typically 6.5 cm long and 5 cm wide at its largest dimensions. In other embodiments, these dimensions may vary within reasonable limits; say 6 cm to 7 cm in length and 4.5 cm to 5.5 cm in width. The absorbent layer is typically 0.5 cm thick and, as the liquid impermeable layer has negligible thickness, the pad 3 is also typically 0.5 cm thick overall. Again, in other embodiments, the thickness of the pad 3 might be between say 0.3 cm to 0.7 cm.

The sheath 4 is tubular and extends from the outward end 6 of the plug 2 to the pad 3. More specifically, the sheath 4 comprises a tube of absorbent material with a layer of liquid impermeable material on its inside surface. In other words, there is a tube of liquid impermeable material inside the tube of absorbent material. The tube of absorbent material extends to the inward surface 10 of the pad 3. Indeed, the absorbent material of the sheath 4 can be integral with the absorbent layer of the pad 3. The tube of liquid impermeable material extends through the pad 3 to the outward surface 11 of the pad 3. Indeed, the tube of liquid impermeable material can be integral with the liquid impermeable backing of the pad 3.

The tube of liquid impermeable material and hence the sheath 4 is open on the outward surface 11 of the pad 3. An opening 12 formed by the sheath 4 on the outward surface 11 of the pad 3 can be seen in FIG. 4B. In this embodiment, the tube of liquid impermeable material is closed where it joins the plug 2. This prevents liquid absorbed by the plug 2 passing into the inside of the sheath 4.

The sheath 4 extends for around 2.5 cm from the outward end of the plug 2 to the inward surface of the pad 3, although in other embodiments this length may vary from say 2 cm to 3 cm. This length is enough to accommodate the tip of say an index finger to allow manipulation of the plug 2.

The diameter of the sheath 4 is smaller than that of the plug 2. More specifically, the external diameter of the sheath 4 at its smallest dimension might be 0.4 cm, although this might vary from say 0.2 cm to 0.8 cm in other embodiments. The small diameter is required to improve the comfort of the product 1 in the region of the vaginal orifice. However, this small diameter is clearly too small to allow a finger to be accommodated inside the sheath 4. The sheath 4 is therefore expandable in a radial direction. This is accomplished by the sheath 4 being elastic in the radial direction. In one embodiment, an elastic tube (not shown) is provided between the absorbent tube and the liquid impermeable tube of the sheath 4. In other embodiments, either or both of the absorbent and liquid impermeable tubes of the sheath 4 are themselves elastic.

The pad 3 is compressed to weaken it along a line 7 that runs along the major axis of the pad 3 all the way from the broad end 8 to the narrow end 9. This line 7 of weakness basically bisects the pad 3. To be precise, the line 7 runs through the opening 12 formed by the sheath 6 and therefore can be considered to be two lines, but it is referred to as a single line in this document for simplicity.

The line is around 0.2 cm to 0.5 cm wide and around 0.2 cm thick (e.g. the compressed cotton of the pad 3 is further compressed to around 0.2 cm thick), although other similar dimensions might be equally suitable. In other embodiments of the invention, the line might be a crease or fold.

A string 13 is provided to aid removal of the product. In this embodiment, the string extends inside the sheath 4 from the outward end of the plug 2 and out through the opening 12. It is approximately 6 cm long.

Figure 5:
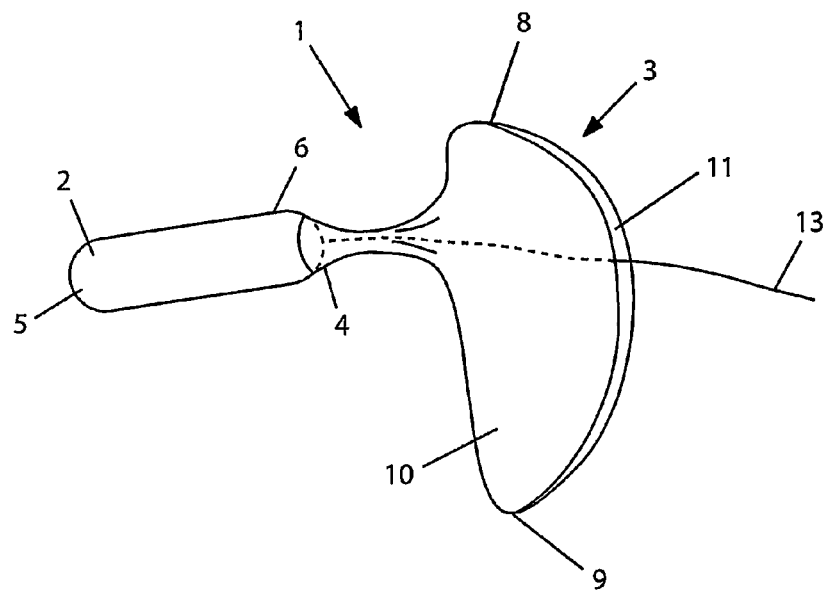
FIG. 5 is a side view of the sanitary product of FIG. 1 with the pad folded as configured for use.

In use, the sanitary product 1 is removed from its packaging and the pad 3 is gently folded around the line 7 of weakness away from the inward surface 10 of the pad 3 (and toward the outward surface 11 of the pad 3), as shown in FIG. 5. One of the wearer's fingers is then inserted in the sheath 4 through the opening 12 to the outward end 6 of the plug 2. The elasticity of the sheath 4 allows it to expand radially and accommodate the finger.

The wearer orients the sanitary product 1 such the plug 2 extends longitudinally toward the vagina, the broad end 8 of the pad 3 is positioned approximately at the rear of the vagina, i.e. toward the anus, and the narrow end 9 of the pad 3 is positioned approximately at the front of the vagina, i.e. toward the pubic bone. The line 7 of weakness is therefore oriented in approximately the same direction and at approximately the same position as the length of the vulva.

The plug 2 is aligned with the vaginal orifice and inserted through the vaginal orifice and into the vaginal cavity. The plug 2 is pushed into the vaginal cavity until the inward surface 10 of the pad 3 comes to rest against the surface of the vagina or, more specifically, the vulva, between the labia majora. This further encourages the pad 3 to fold around the line 7 of weakness and conform to the shape of the vulva. The finger is then withdrawn from the sheath 4, leaving the sanitary product 1 in place.

During use, menstrual liquid is absorbed by the plug 2. Excess liquid is also drawn along the absorbent layer of the sheath 4 and absorbed by the pad 3. The product 1 has enough absorptive capacity to handle all but extremely excessive flows of menstrual fluid. However, the dimensions of the plug 2 mean that women have very little awareness of having the product 1 in place. The small diameter of the sheath 4 avoids any significant pressure being exerted on the vaginal orifice, which again improves comfort. Finally, the dimensions and shape of the pad 3 mean that it resides between the labia majora and is comfortable and unobtrusive.

Figure 6:
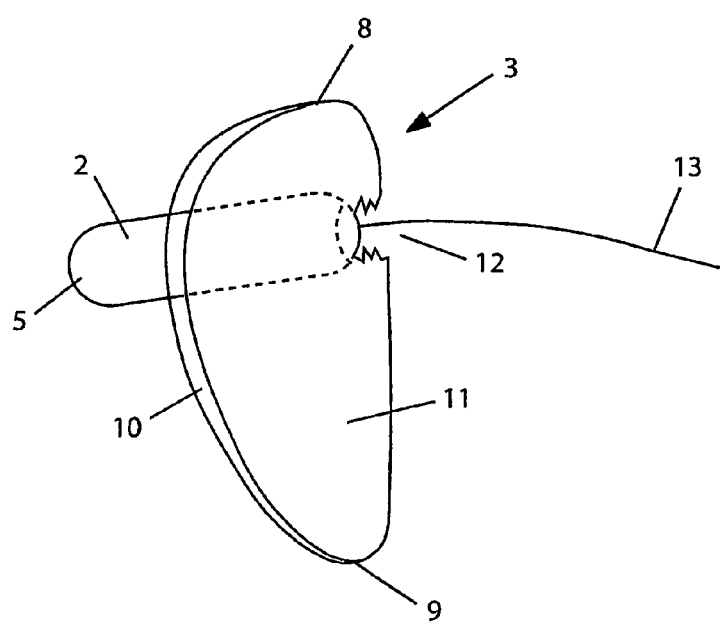
FIG. 6 is a side view of the sanitary product of FIG. 1 during removal of an internally worn plug of the sanitary product after use.

When it is desired to remove the product 1, the wearer can grasp the string 13 and pull it to remove the plug 2 from the vaginal cavity. As the plug 2 is pulled out of the vaginal cavity, the pad 3 folds around the line 7 of weakness in a direction opposite to that in which it is folded in use, e.g. toward the inward surface 10 of the pad 3 (and away from the outward surface 11 of the pad 3), as shown in FIG. 6. In other words, the outward surface 11 of the pad 3 is pushed or grasped by the wearer to fold the pad 3 over the plug 2 and sheath 4 and the inward surface 10 effectively becomes enclosed by the outward surface 11.

Figure 7:
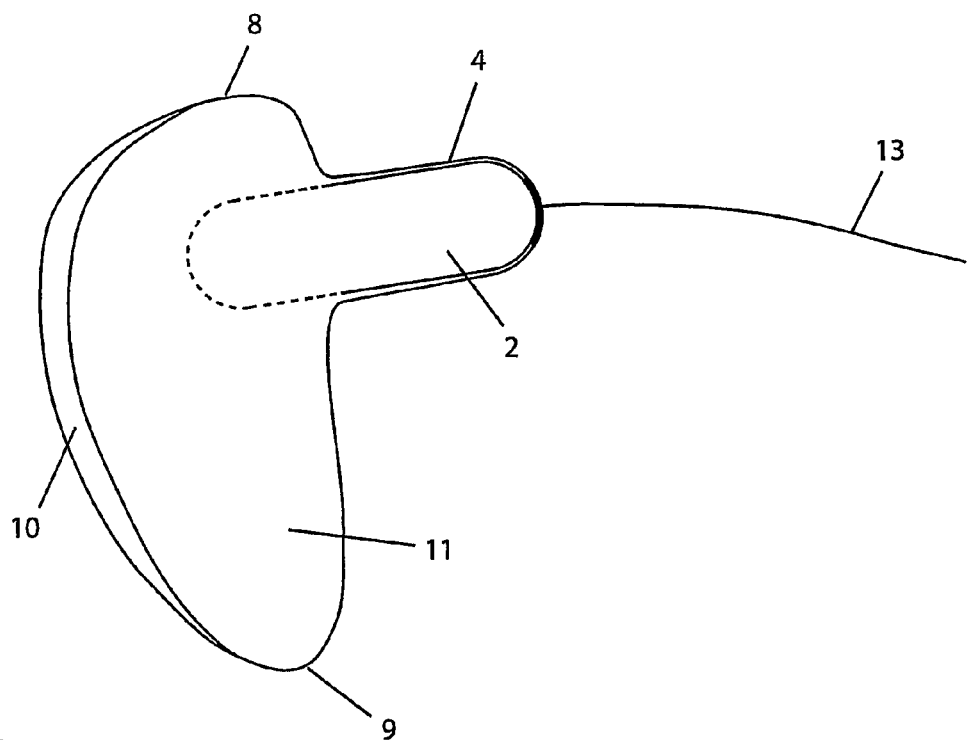
FIG. 7 is a side view of the sanitary product of FIG. 1 after removal of the plug.

In addition, the sheath 4 can expand radially to accommodate the plug 2. More specifically, pulling the string 13 causes the plug 2 to invert the sheath 4. The inverted sheath 4 expands in a similar way to when accommodating the wearer's finger during insertion and allows the plug 2 to be drawn into the inverted sheath 4, as shown in FIG. 7. So, with the plug 2 accommodated, at least partially, in the inverted sheath 4 and the pad 3 folded over the plug 2, the entire sanitary product 1 is enclosed by the liquid impermeable layer of the outward surface 11 of the pad 3 and the sheath 4. This liquid impermeable layer does not come into contact with the vagina at any time and is therefore relatively clean. The wearer need only touch the string 13 and this liquid impermeable layer during removal and disposal of the sanitary product 1. So, the sanitary product 1 can be hygienically removed and disposed of after use.

Figure 8:
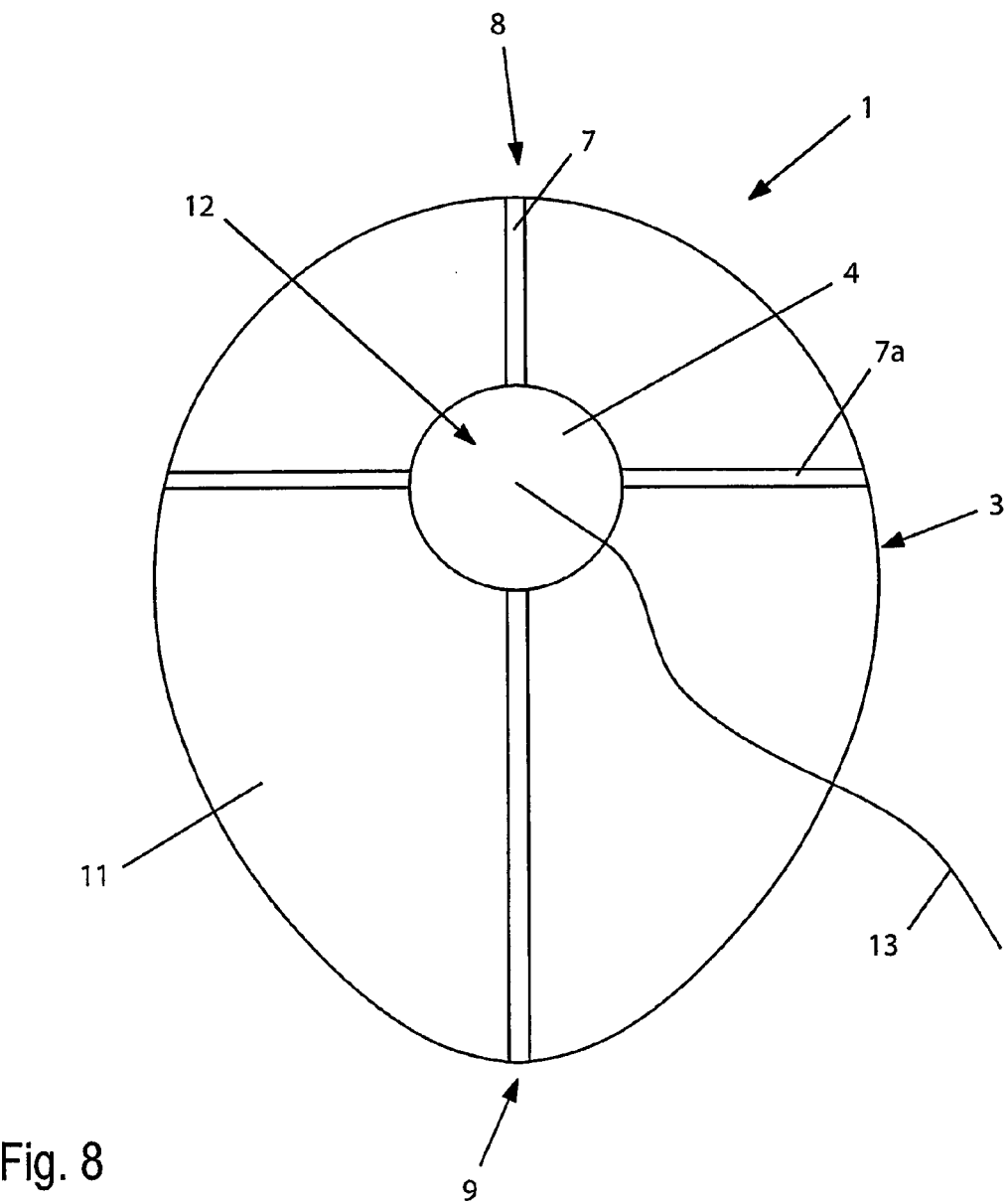
FIG. 8 is a rear view of a sanitary product according to another embodiment of the invention.

Referring to FIG. 8, in another embodiment, the sanitary product 1 has a second line of weakness 7a in addition to the first line of weakness 7 of the embodiment of the sanitary product described above. The other features of the sanitary product 1 are the same and therefore labelled with the same reference numerals. The second line of weakness 7a is perpendicular to the first line of weakness 7 and allows the pad 3 to fold about its width. More specifically, the second line of weakness 7a is oriented across the width of the pad 3 at the location of the plug 2 (or the position of the opening 12 through the pad 3). Indeed, in this embodiment, the second line of weakness is coincident with the minor axis of the elliptical shape of the pad 3.

The second line of weakness 7 allows the pad to be folded away from the opening of the urethra whilst the sanitary product 1 is generally in position or in use, e.g. whilst the plug 2 is inserted in the vagina. This can allow the user to urinate with the sanitary product 1 in position. It also allows the pad 3 to fold into quadrants during removal of the pad 3, which means that the pad 3 can fold around the plug 2 more neatly.

The described embodiments of the invention are only examples of how the invention may be implemented. Modifications, variations and changes to the described embodiments will occur to those having appropriate skills and knowledge. These modifications, variations and changes may be made without departure from the spirit and scope of the invention defined in the claims and its equivalents.

The invention claimed is:

1. A sanitary product comprising:
an absorbent plug configured for absorption and storage of bodily fluids wearable inwardly of a vaginal orifice;
an absorbent pad configured for absorption and storage of bodily fluids wearable outwardly of the vaginal orifice, wherein the pad has at least one line of weakness about which it is configured to fold over the plug upon removal from the vagina when in use; and
a liquid impermeable flexible sheath having an open proximal end and a closed distal end, said absorbent plug joined to the distal end of the sheath, and said proximal end joined to said absorbent pad,
wherein the distal end of the sheath is closed such that liquid cannot pass from the plug to an inside of the sheath,
wherein the proximal end of said sheath opens through the pad such that a wearer's finger can be received into the sheath to assist insertion of the plug into the vagina,
and wherein said sheath is liquid impermeable in a direction when located inside the vagina from an exterior of the sheath to an interior of the sheath.

2. The sanitary product of claim 1, wherein a line of weakness is substantially coincident with the length of the pad.

3. The sanitary product of claim 1, wherein a line of weakness is substantially transverse to the length of the pad.

4. The sanitary product of claim 1, wherein the line of weakness substantially bisects the pad.

5. The sanitary product of claim 1, wherein the pad has two or more lines of weakness about which it is disposed to fold.

6. The sanitary product of claim 1, wherein the line of weakness is a line of compression of the pad.

7. The sanitary product of claim 1, wherein the line of weakness is a crease.

8. The sanitary product of claim 1, wherein the sheath comprises a tube of liquid impermeable material.

9. The sanitary product of claim 8, wherein the pad comprises an absorbent layer and a liquid impermeable backing sheet and the backing sheet is integral with the liquid impermeable material of the sheath.

10. The sanitary product of claim 1, wherein the sheath passes liquid along its length from the plug to the pad.

11. The sanitary product of claim 1, wherein the sheath comprises a tube of absorbent material.

12. The sanitary product of claim 1, wherein the sheath comprises a tube of liquid impermeable material inside a tube of absorbent material.

13. The sanitary product of claim 1, wherein the sheath has a smaller diameter than that of the plug.

14. The sanitary product of claim 1, wherein the sheath is resiliently expandable in a radial direction to receive a finger during insertion of the product into the vagina.

15. The sanitary product of claim 1, wherein the sheath is not significantly expandable in a longitudinal direction.

16. The sanitary product of claim 1, wherein the sheath extends for about 2.5 cm between an end of the plug and a surface of the pad closest to the plug.

17. The sanitary product of claim 1, further comprising a cord having a proximal end and a distal end, said proximal end attached to the plug or distal end of the sheath to assist removal of the plug from the vagina.

18. The sanitary product of claim 17, wherein the cord is configured such that when the plug is located inside the vagina, the cord passes along the interior of the sheath from its distal end and exits the sheath through the opening in the proximal end of the sheath with the proximal end of the cord located outside the sheath, such that the cord can be used to assist removal of the plug from the vagina by pulling the plug from the vagina by the cord.

19. The sanitary product of claim 1, wherein the plug is about 4 cm in length or less and 2 cm in diameter or less.

20. The sanitary product of claim 1, wherein the plug is about 3.5 cm in length or less and 1.5 cm in diameter or less.

21. The sanitary product of claim 1, wherein the plug is about 3.5 cm in length and 1.5 cm in diameter.

22. The sanitary product of claim 1, wherein the pad has the shape of a flat ellipse with one end wider than the other.

23. The sanitary product of claim 1, wherein the pad is about 6.5 cm long and 5.5 cm wide.

24. The sanitary product of claim 1, wherein the pad is about 0.5 cm thick.

25. The sanitary product of claim 1 is manufactured by a method comprising joining the absorbent plug wearable internally of the vaginal orifice to the absorbent pad wearable externally of the vaginal orifice and providing the pad with a line of weakness about which it is disposed to fold.

26. A method of using the sanitary product of claim 1, comprising withdrawing the plug through the sheath and folding the pad around the plug.

\* \* \* \* \*